United States Patent
Wyatt et al.

(10) Patent No.: US 8,631,806 B2
(45) Date of Patent: Jan. 21, 2014

(54) MASCARA SYSTEM WITH THICKENING BENEFITS

(75) Inventors: Peter Jonathan Wyatt, Forest Hill, MD (US); Bryan Michael Kadlubowski, Manchester, MD (US); Thomas Elliott Rabe, Baltimore, MD (US); Stephen Robert Glassmeyer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/295,711

(22) Filed: Nov. 14, 2011

(65) Prior Publication Data

US 2012/0060859 A1    Mar. 15, 2012

Related U.S. Application Data

(63) Continuation of application No. 12/481,318, filed on Jun. 9, 2009, now Pat. No. 8,066,015, which is a continuation of application No. 11/436,240, filed on May 18, 2006, now Pat. No. 7,632,489, which is a continuation-in-part of application No. 11/132,818, filed on May 19, 2005, now abandoned.

(51) Int. Cl.
*A45D 40/26* (2006.01)

(52) U.S. Cl.
USPC .......................................... 132/218; 424/70.7

(58) Field of Classification Search
USPC .......... 132/218, 317, 318, 320, 208; 424/70.7
See application file for complete search history.

(56) References Cited

U.S. PATENT DOCUMENTS

| | | |
|---|---|---|
| 210,274 A | 11/1878 | Stohlmann |
| 299,390 A | 5/1884 | Hyatt |
| 1,982,838 A | 12/1934 | Sunnen |
| 2,592,296 A | 4/1952 | Kutik |
| 2,651,810 A | 9/1953 | Snyder |
| 3,111,253 A | 11/1963 | Hennessey |
| 3,618,154 A | 11/1971 | Muhler |
| 3,680,750 A | 8/1972 | Franco |
| 3,892,248 A | 7/1975 | Kingsford |
| 3,896,823 A | 7/1975 | Spatz |
| 4,422,986 A | 12/1983 | Cole |
| 4,461,312 A | 7/1984 | Gueret |
| 4,498,490 A | 2/1985 | Seidler |
| 4,565,205 A | 1/1986 | Taylor |

(Continued)

FOREIGN PATENT DOCUMENTS

| DE | 237807 | 3/1909 |
|---|---|---|
| DE | 10102219 A1 | 7/2002 |

(Continued)

*Primary Examiner* — Rachel Steitz
(74) *Attorney, Agent, or Firm* — John G. Powell; Charles R. Ware

(57) ABSTRACT

A mascara system comprising, in combination: (a) a mascara applicator comprising a substantially longitudinal stem having a major axis A and a plurality of protrusions extending therefrom, wherein at least two adjacent protrusions are spaced from one another at a distance R at the base of the stem; (b) a mascara composition comprising primary particles that are at least about 5 microns in equivalent diameter; and (c) a dermatologically acceptable carrier. The mascara applicator is a molded applicator, the distance R is from about 0.75 mm to about 3.0 mm, and at least one of the primary particles is a wax primary particle composed primarily of one or more waxes.

14 Claims, 4 Drawing Sheets

(56) References Cited

U.S. PATENT DOCUMENTS

| | | |
|---|---|---|
| 4,635,659 A | 1/1987 | Spatz |
| 4,660,582 A | 4/1987 | Taylor |
| 4,804,004 A | 2/1989 | Taylor |
| 4,815,608 A | 3/1989 | Silberberg |
| 4,861,179 A | 8/1989 | Schrepf |
| 4,863,026 A | 9/1989 | Perkowski |
| 4,887,622 A | 12/1989 | Gueret |
| 4,898,195 A | 2/1990 | Sussman |
| 4,944,937 A | 7/1990 | McCall |
| 4,964,429 A | 10/1990 | Cole |
| 4,982,838 A | 1/1991 | Fitjer |
| 4,993,440 A | 2/1991 | Gueret |
| 5,030,446 A | 7/1991 | Russ et al. |
| 5,161,554 A | 11/1992 | Fitjer |
| 5,224,787 A | 7/1993 | Vasas |
| 5,531,582 A | 7/1996 | Klinkhammer |
| 5,557,871 A | 9/1996 | LaLonde |
| 5,593,680 A | 1/1997 | Bara |
| 5,612,021 A | 3/1997 | Mellul |
| 5,618,523 A | 4/1997 | Zysman |
| 5,620,693 A | 4/1997 | Piot |
| 5,637,291 A | 6/1997 | Bara |
| 5,762,432 A | 6/1998 | Dunleavy |
| 5,773,611 A | 6/1998 | Zysman |
| 5,846,550 A | 12/1998 | Perrin |
| 5,849,278 A | 12/1998 | Piot |
| 5,853,011 A | 12/1998 | Gueret |
| 5,860,432 A | 1/1999 | Gueret |
| 5,882,657 A | 3/1999 | Miguel |
| 5,911,226 A | 6/1999 | Vecchiola |
| 5,914,117 A | 6/1999 | Lavaud |
| 5,925,337 A | 7/1999 | Arraudeau |
| 5,955,091 A | 9/1999 | Hansenne |
| 6,062,757 A | 5/2000 | Gueret |
| 6,146,649 A | 11/2000 | Hansenne |
| 6,200,051 B1 | 3/2001 | Gueret |
| 6,241,411 B1 | 6/2001 | Brieva et al. |
| 6,260,558 B1 | 7/2001 | Neuner |
| 6,274,131 B1 | 8/2001 | Piot |
| 6,289,902 B1 | 9/2001 | Mathiez |
| 6,314,967 B1 | 11/2001 | Castells Ribas |
| 6,327,736 B1 | 12/2001 | Schaefer |
| 6,343,607 B1 | 2/2002 | Gueret |
| 6,375,941 B1 | 4/2002 | Piot et al. |
| 6,412,139 B1 | 7/2002 | Weihrauch |
| 6,412,496 B1 | 7/2002 | Gueret |
| 6,432,421 B1 | 8/2002 | Brown |
| 6,461,621 B1 | 10/2002 | Gagnebien |
| 6,464,920 B1 | 10/2002 | Krämer |
| 6,494,215 B2 | 12/2002 | Gueret |
| 6,497,458 B2 | 12/2002 | Batson |
| 6,546,937 B2 | 4/2003 | Gueret |
| 6,581,610 B1 | 6/2003 | Gueret |
| 6,591,842 B2 | 7/2003 | Gueret |
| 6,616,366 B1 | 9/2003 | Weihrauch |
| 6,681,777 B2 | 1/2004 | Gueret |
| 6,739,345 B2 | 5/2004 | Stanley |
| 6,793,940 B2 | 9/2004 | Tournilhac |
| 6,814,084 B2 | 11/2004 | Gueret |
| 6,866,149 B2 | 3/2005 | Alzner |
| 6,871,373 B2 | 3/2005 | Driesen |
| 7,029,662 B2 * | 4/2006 | Auguste et al. ............. 424/70.7 |
| 7,069,936 B2 | 7/2006 | Gueret |
| 7,138,110 B2 | 11/2006 | Auguste |
| 7,211,244 B2 | 5/2007 | Auguste |
| 7,219,801 B2 | 5/2007 | Christian |
| 7,226,555 B2 | 6/2007 | Weihrauch |
| 7,261,483 B2 | 8/2007 | Gueret |
| 7,294,297 B2 | 11/2007 | Weihrauch |
| 7,325,550 B2 | 2/2008 | Eckers |
| 7,347,993 B2 | 3/2008 | Bracken |
| 7,374,358 B2 | 5/2008 | Neuner |
| 7,422,018 B2 | 9/2008 | Dieudonat |
| 7,481,227 B2 | 1/2009 | De Laforcade |
| 7,481,592 B2 | 1/2009 | Gueret |
| 7,503,093 B2 | 3/2009 | Weihrauch |
| 7,581,546 B2 | 9/2009 | Dumler |
| 7,632,489 B2 | 12/2009 | Wyatt |
| 7,644,466 B2 | 1/2010 | Weihrauch |
| 7,789,094 B2 | 9/2010 | Gueret |
| 7,886,397 B2 | 2/2011 | Gueret |
| 2002/0014250 A1 | 2/2002 | Gueret |
| 2002/0018760 A1 | 2/2002 | Vatter |
| 2002/0020424 A1 | 2/2002 | Gueret |
| 2002/0023657 A1 | 2/2002 | Gueret |
| 2002/0192250 A1 | 12/2002 | Chevalier |
| 2003/0031640 A9 | 2/2003 | De La Poterie |
| 2003/0059388 A1 | 3/2003 | Auguste |
| 2003/0064038 A1 | 4/2003 | Auguste |
| 2003/0064045 A1 | 4/2003 | Auguste |
| 2003/0080463 A1 | 5/2003 | Harris |
| 2003/0091521 A1 | 5/2003 | Midha |
| 2003/0147828 A1 | 8/2003 | Bracken |
| 2003/0163884 A1 | 9/2003 | Weihrauch |
| 2003/0234208 A1 | 12/2003 | Huang |
| 2004/0009201 A1 | 1/2004 | Collin |
| 2004/0022752 A1 | 2/2004 | De La Poterie |
| 2004/0057973 A1 | 3/2004 | Wittkowski |
| 2004/0091447 A1 | 5/2004 | Pays |
| 2004/0137020 A1 | 7/2004 | De La Poterie |
| 2004/0137021 A1 | 7/2004 | De La Poterie |
| 2004/0142008 A1 | 7/2004 | Chevalier |
| 2004/0142831 A1 | 7/2004 | Jager Lezer |
| 2004/0186030 A1 | 9/2004 | Hofrichter |
| 2004/0191200 A1 | 9/2004 | Lezer |
| 2004/0226573 A1 | 11/2004 | Gueret |
| 2005/0006819 A1 | 1/2005 | Weihrauch |
| 2005/0034740 A1 | 2/2005 | Eckers |
| 2005/0065046 A2 | 3/2005 | Jager Lezer |
| 2005/0115011 A1 | 6/2005 | Petit |
| 2005/0160546 A1 | 7/2005 | Weihrauch |
| 2005/0169949 A1 | 8/2005 | De La Poterie |
| 2005/0172439 A1 | 8/2005 | Weihrauch |
| 2005/0175648 A1 | 8/2005 | De La Poterie |
| 2005/0238598 A1 | 10/2005 | Aubert |
| 2005/0247587 A1 | 11/2005 | Holland |
| 2006/0002758 A1 | 1/2006 | Gueret |
| 2006/0056903 A1 | 3/2006 | Gueret |
| 2006/0070635 A1 | 4/2006 | Dumler |
| 2006/0099231 A1 | 5/2006 | De La Poterie |
| 2006/0128578 A9 | 6/2006 | Jager Lezer |
| 2006/0134038 A1 | 6/2006 | De la Poterie |
| 2006/0257343 A1 | 11/2006 | Mori |
| 2006/0260633 A1 | 11/2006 | Wyatt |
| 2006/0272666 A1 | 12/2006 | Wyatt |
| 2006/0272668 A1 | 12/2006 | Wyatt |
| 2006/0289027 A1 | 12/2006 | Wyatt |
| 2007/0175788 A1 | 8/2007 | Holba |
| 2007/0192979 A1 | 8/2007 | Knopow |
| 2008/0060669 A1 | 3/2008 | Malvar |
| 2008/0083421 A1 | 4/2008 | Malvar |
| 2008/0115798 A1 | 5/2008 | Rainey |
| 2008/0219748 A1 | 9/2008 | Salciarini |
| 2009/0241980 A1 | 10/2009 | Wyatt |
| 2010/0028283 A1 | 2/2010 | Mori |
| 2010/0272766 A1 | 10/2010 | Vatter |

FOREIGN PATENT DOCUMENTS

| | | |
|---|---|---|
| DE | 10130863 A1 | 2/2003 |
| DE | 10201635 A1 | 7/2003 |
| DE | 10212701 A1 | 10/2003 |
| DE | 10221869 A | 11/2003 |
| EP | 0038524 B1 | 8/1985 |
| EP | 0075051 B1 | 11/1986 |
| EP | 0474934 A1 | 3/1992 |
| EP | 0753295 B1 | 4/1998 |
| EP | 0905206 A3 | 1/2001 |
| EP | 1161896 A1 | 12/2001 |
| EP | 01157632 B2 | 3/2003 |
| EP | 1329213 A1 | 7/2003 |
| EP | 1384417 A2 | 1/2004 |
| EP | 01454561 A1 | 9/2004 |
| EP | 1607020 A1 | 12/2005 |

(56) References Cited

FOREIGN PATENT DOCUMENTS

| | | | |
|---|---|---|---|
| EP | 1649893 A | 4/2006 |
| EP | 1070468 B1 | 2/2008 |
| EP | 1632149 B1 | 12/2008 |
| FR | 2788969 A1 | 8/2000 |
| FR | 2827168 A | 1/2003 |
| JP | 02062817 A | 3/1990 |
| JP | 10338612 A | 12/1998 |
| JP | 11060440 A | 3/1999 |
| JP | 2000072645 A | 3/2000 |
| JP | 2000319127 A | 11/2000 |
| JP | 2002020235 A | 1/2002 |
| JP | 2004107235 A | 4/2004 |
| JP | 2004315420 A2 | 11/2004 |
| JP | 2005125021 | 5/2005 |
| WO | WO9831605 | 7/1998 |
| WO | WO9931184 A1 | 6/1999 |
| WO | WO0158420 | 8/2001 |
| WO | WO0203931 A | 1/2002 |
| WO | WO02056726 A2 | 7/2002 |
| WO | WO0203931 A3 | 10/2002 |
| WO | WO03075881 A1 | 9/2003 |
| WO | WO2004022010 A8 | 3/2004 |
| WO | WO2004087078 A | 10/2004 |
| WO | WO2006125122 | 11/2006 |

* cited by examiner

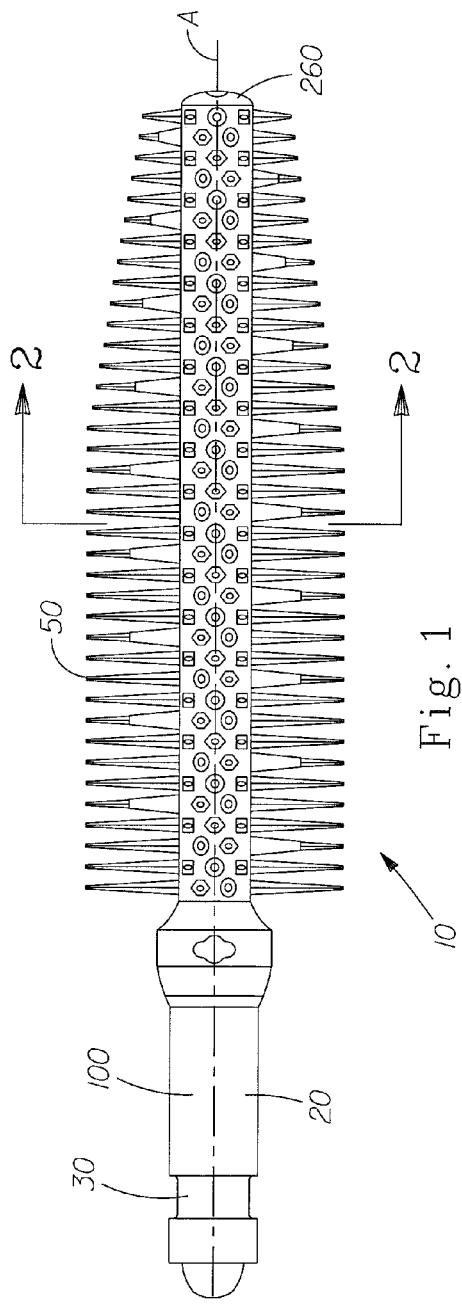
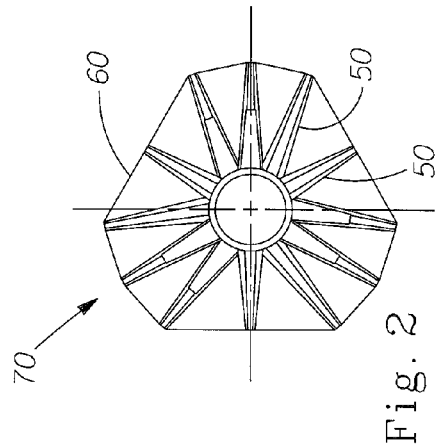
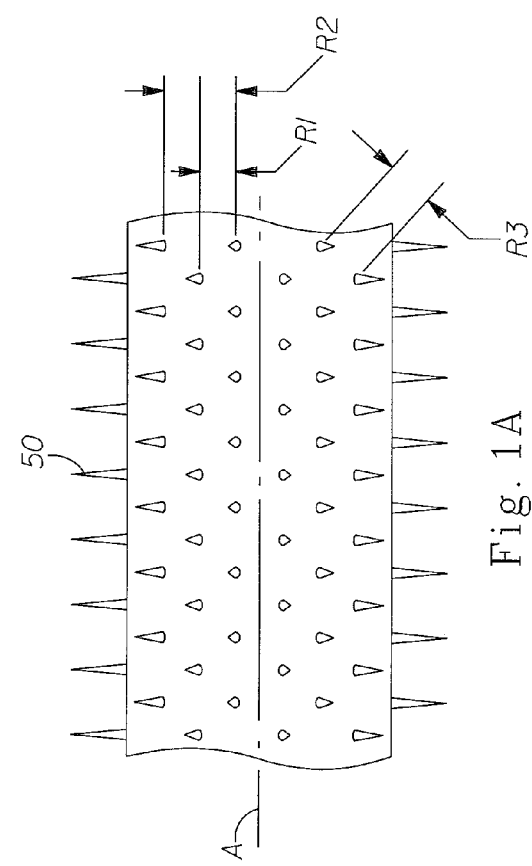
Fig. 1
Fig. 2
Fig. 1A

MASCARA SYSTEM WITH THICKENING BENEFITS

CROSS REFERENCE TO RELATED APPLICATION

This application is a continuation of U.S. application Ser. No. 12/481,318, filed on Jun. 9, 2009 now U.S. Pat. No. 8,066,015, which is a continuation of U.S. application Ser. No. 11/436,240, filed on May 18, 2006, now U.S. Pat. No. 7,632,489, which is a continuation-in-part of U.S. application Ser. No. 11/132,818, filed May 19, 2005, now abandoned.

FIELD OF THE INVENTION

The present invention relates to a cosmetic system containing a cosmetic composition comprising one or more particle types for coating the lashes in combination with a particularly designed molded applicator for use in the cosmetic field on keratinous fibers, particularly for making up the eyelashes and eyebrows.

BACKGROUND OF THE INVENTION

Mascaras are a major cosmetic product of significant importance to the cosmetic industry. They are used to enhance the beauty of a person's eyes by coating the eyelashes, and in some cases, the eyebrows, to primarily thicken, lengthen, color, curl, and define the individual lashes.

Mascaras come in a variety of forms including cakes or blocks, creams, gels, semi-solids, and low viscosity liquids. Cake mascaras were originally the most popular form consisting of at least 50% soap with the pigment mixed in with the soap cakes. With a wet brush, the mascara could be lathered and then applied to the lashes resulting in a satisfactory smooth application, but with a thin cosmetic coating on the individual lashes. The primary drawback was that the film on the lashes was very water soluble and prone to smudging and running on the skin around the perimeter of the eye. As a resolution, waxes were incorporated into mascara compositions thereby improving their water-resistant properties. Unfortunately, the smoothness of the application was adversely affected. That is, as the viscosity of the mascara formulation increased, it became increasingly harder to apply, messier, and yielded less separation of the lashes.

With the advent of mascara applicators (formerly referred to as "automatic" applicators) a means for expanding formulation options for mascaras came into existence. Creams, for example, combined with a twisted metal wire brush or wand application provided a convenient use and composition that enabled the incorporation of film formers to improve the rubbing resistance and flexibility of mascara films. This also allowed a convenient implement to separate and build the lashes. Today, there are several types of mascara formulations including anhydrous, water-in-oil emulsions, oil-in-water emulsions, and water-based mascaras that contain little or no oil phase. The emulsions, previously mentioned, may also be multiple emulsions for example, but not limited to water-in-oil-in-water emulsion. Many mascaras are water-based emulsions and contain emulsified waxes and polymers usually with pigments dispersed into the water phase. The water provides curling and application properties, while the waxes and polymers create the transfer resistant end mascara film on the lash that is colored by the pigments. Anhydrous and water-in-oil mascaras are generally referred to as waterproof mascaras, as they have superior transfer resistance, especially to water. Their high content of hydrophobic materials creates a film which contains very little materials that allow water to break up the film and make it wear away. In the case of the water-in-oil mascaras, the internal droplets of water can deliver water-soluble/dispersible materials that would otherwise not be able to be incorporated into an oily phase. The water-based mascaras are typically gelled water with a polymer to create deposition and hold of the lashes. These mascaras usually do not have colorants, although colorants can be added in.

Consumers expect particular properties from their mascara products such as adhesion to the lashes, lengthening/curling of the lashes, lack of smudging or flaking, thick lashes, and good separation of clumps of lashes. Particularly, the desire is for long, luscious, full, soft, and separated lashes. Mascaras generally distribute a smooth and relatively thin (coating thickness) film over the eyelashes producing a satisfactory array of reasonably separated lashes that are darker and thicker than bare lashes, making the eyes more noticeably beautiful. It is well understood that some lash clumping will naturally occur since lashes are arranged in both rows and columns above and below one's eye. Therefore, "reasonably separated" lashes are not necessarily envisioning every lash as a single entity. Mascara that is deemed by a user to separate well will leave more clumps of lashes than mascara that is deemed not to separate lashes well. Typically, the deposition of mascara has a coating that is 5-15 microns thick. Many "volumizing" mascaras, however, are messy and clumpy and tend to clump too many lashes together in a thick, less separated look which gives the look of fewer lashes.

Notwithstanding the above, the present inventors have found a system which combines a large particle-containing mascara composition in combination with a molded applicator that is designed in such a way as to allow large particle transfer and compositions comprising the same in addition to sufficient lash combing. Such combination will thicken the diameter of lashes while keeping them well separated, leaving the appearance of thick, well-separated, and beautiful lashes.

SUMMARY OF THE INVENTION

In order to provide a solution to the foregoing problems, at least one embodiment herein disclosed herein is directed to a mascara system comprising, in combination, a molded, thermoplastic mascara applicator and a mascara composition. The applicator comprises a substantially longitudinal stem having a major axis and a plurality of protrusions extending therefrom. At least two adjacent protrusions are spaced from one another at a distance of from about 0.75 mm to about 3.0 mm at the base of the stem. The mascara composition comprises primary particles and secondary particles. The primary particles are at least about 5 microns in equivalent diameter, and at least some of the primary particles are pigment particles. At least some of the secondary particles are fibers that have a length of between about 1 micron and about 100 microns and a length to diameter ratio of between about 3.5:1 and about 500:1. The mascara composition also comprises a dermatologically acceptable carrier.

BRIEF DESCRIPTION OF THE DRAWINGS

FIG. 1 is a side view of an embodiment of a brush according to the invention;

FIG. 1-A is a fragment of a side view of an embodiment of a brush according to the invention showing differential spacing of adjacent protrusions;

FIG. 2 is a cross-sectional view of the brush of FIG. 1, taken along lines 2-2.

DETAILED DESCRIPTION OF THE INVENTION

Figure 3:
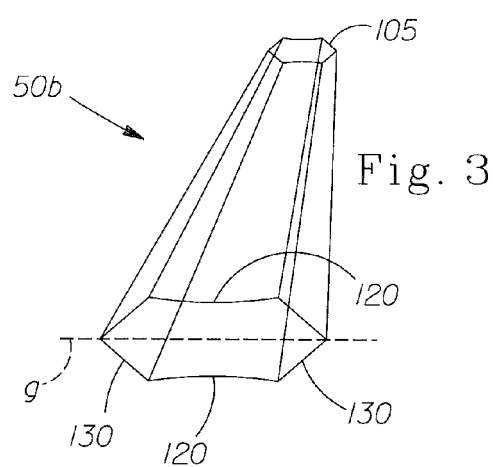
FIGS. 3 to 6 are perspective views of various embodiments of selected protrusions of the brush of the present invention.

While the specification concludes with the claims particularly pointing out and distinctly claiming the invention, it is believed that the present invention will be better understood from the following description.

As used herein, "comprising" means that other steps and ingredients can be added. This term encompasses the terms "consisting of" and "consisting essentially of". The phrase "consisting essentially of" means that the composition may include additional ingredients, but only if the additional ingredients do not materially alter the basic and novel characteristics of the claimed compositions or methods.

All percentages, parts and ratios are based upon the total weight of the topical compositions of the present invention and all measurements made are at 25° C., unless otherwise specified. All such weights as they pertain to listed ingredients are based on the active level and, therefore; do not include carriers or by-products that may be included in commercially available materials, unless otherwise specified.

The term "specific gravity," unless otherwise noted, is the specific gravity of the particle calculated based on the mass and volume exhibited by the particles themselves. For example, in determining the specific gravity of a hollow particle, the volume of the particle is calculated using the outer-shell diameter. The specific gravity is not a bulk specific gravity which includes volume contributions from voids in between particles. It is the average specific gravity of the individual particles. Methods for measuring specific gravity of particles are well disclosed in the art.

The term "make-up" refers to products that leave color on the face, including on the eyelashes, eyebrows, cheeks, lips, etc. . . .

As used herein, the term "keratinous fibers" refers particularly to mammalian (e.g., human or animal) hair such as hair on the head or body, brows and eyelashes.

"Protrusions," as used herein, refers to surface extensions that protrude from the stem of the cosmetic applicator of the present invention. The protrusions may extend perpendicularly or at an angle relative to the major axis A. If the protrusions are aligned in a row on the stem, the angle of the protrusions may be the same as the angle of the adjacent protrusion within that row. The protrusions are intended to pass between adjacent keratinous fibers as the applicator is stroked across the keratinous fibers, particularly lashes. In the case of mascara compositions, the primary function of protrusions is to deposit mascara on the lashes and separate lashes.

The term "dermatologically-acceptable," as used herein, means that the compositions or components thereof so described are suitable for use in contact with mammalian keratinous tissue without undue toxicity, incompatibility, instability, allergic response, and the like.

The term "safe and effective amount" as used herein means an amount of a compound or composition sufficient to significantly induce a positive benefit, preferably a positive keratinous tissue appearance or feel benefit, including independently or in combinations the benefits disclosed herein, but low enough to avoid serious side effects, i.e., to provide a reasonable benefit to risk ratio, within the scope of sound judgment of the skilled artisan.

The compositions of the present invention comprise the following ingredients.

A. Applicator Brush

Conventional mascara applicators are typically composed of a stem formed by helically twist of two strands of metal wire and bristles which are radially implanted into the core and tightly held between the wound metal strands. A principle limitation of such an applicator is that the bristles are randomly positioned and terminate at the wire strands in very close proximity to one another. Each bristle has a varying distance between itself and other bristles as one moves both along the length of the bristle or along the length of the stem.

The applicators of the present invention exhibit a substantially longitudinal stem having a major axis A and a plurality of protrusions extending therefrom; wherein at least two adjacent protrusions are spaced from one another at a distance R at the base of the stem. For example, FIG. 1-A shows differential distances of $R_1$, $R_2$, and $R_3$, generically described as R. The distance R is measured from the base of one protrusion to the base of the adjacent protrusion. This measurement includes, but is not limited to, adjacent protrusions along the major axis, adjacent protrusions vertically positioned from each other, adjacent protrusions positioned diagonally from each other, or adjacent protrusions within a circumference of each other. (FIG. 2) The present invention may R to be from about 0.2 mm, from about 0.5 mm, from about 0.75 mm or from about 0.85 mm but no more than about 1 mm, no more than about 2 mm or no more than about 3 mm. The gaps between the protrusions are engineered to allow for both good quality separation of lashes and the transfer of large particles and compositions thereof, such as those described herein under "Composition", from the applicator to the lashes. Additionally, the protrusions may be oriented in rows along the length of the stem. For example, the protrusions may be oriented such that they are in rows substantially parallel to the major axis A, substantially perpendicular to the major axis A or they may be positioned radially in relation to the major axis A.

FIG. 1 shows, generally, an embodiment of a brush 10 of the present invention comprising a substantially longitudinal core, or stem, 260 having a longitudinal, or major, axis A, and a plurality of protrusions 50 extending therefrom. Each protrusion has a base associated with the stem and a free end opposite to the base. Each protrusion has external walls and a longitudinal axis B oriented along the length of the protrusion (FIG. 5). The walls of the protrusion 50 can be concave, round, planar, or convex, FIGS. 3-5.

The embodiment of FIG. 1 also has an optional stem 20 that, via an optional locking groove 30, that can be attached to a handle (not shown). The brush 10 may be trimmed, to change the length of some protrusions or otherwise form a particular configuration of the brush 10 in a cross-section perpendicular to the major axis A. For example, FIG. 2 shows that the trimming can be made to comprise an envelope curve 60 of approximately triangular shape with rounded or skewed corners 70 so that the protrusions 50 have differential lengths. The same effect can be achieved by using a process of the present invention, and without trimming, as described in co-pending application to Dumler, et al., filed Oct. 1, 2004.

In one embodiment, at least some of the protrusions 50 may have at least one external depression 120 in their walls as described in co-pending application to Dumler, et al., filed Oct. 1, 2004. These protrusions are termed herein as "selected protrusions," because the process of the present invention (described herein below) allows one to design what protrusions should be structured to have at least one external depression. The depressions of the selected protrusions can be oriented in a direction parallel to the longitudinal axes B of the protrusions, or, alternatively or additionally, can be disposed at free ends of the protrusions.

Figure 5:
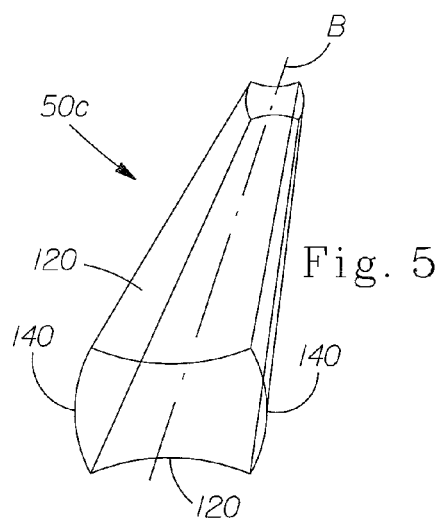
Figure 6:
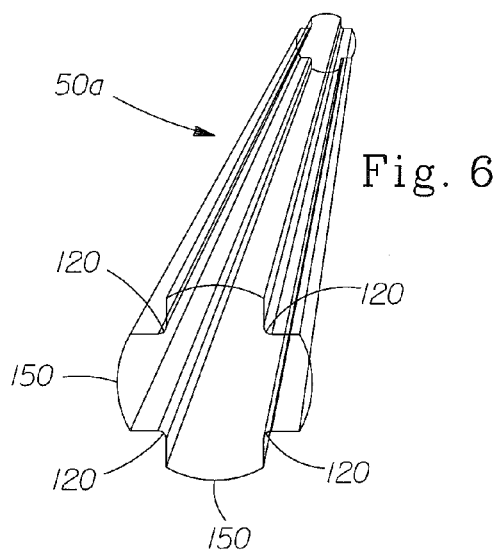

Protrusions 50 can comprise protrusions having a generally round cross-section (FIGS. 4 and 6), protrusions 50b having a generally oblong, or elongated, cross-section (FIGS. 3 and 5), or protrusions having any other suitable general cross-section, for example, polygonal. As used herein, the term "oblong" refers to a geometrical shape that generally has unequal dimensions in two mutually perpendicular directions. The selected protrusion can have any suitable shape in its cross-section perpendicular to the protrusion's longitudinal axis. For example, the selected protrusion can have a cross-section that includes oblong, polygon, circular, trapezoid, or any other shape.

Figure 7:
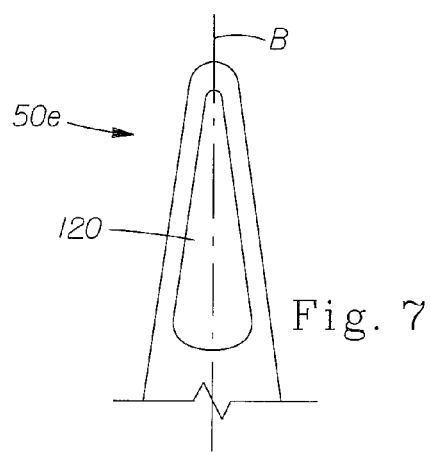
FIG. 7 is a plan view of an exemplary embodiment of the protrusion having a depression intermediate the base of the protrusion and the end thereof.

The number of the depressions 120 per the selected protrusion can vary. For example, the selected protrusion can have one, two, three, four, and more depressions 120. In the selected protrusions having more than one depression 120, the location of the depressions may vary. For example, in the selected protrusions having two depressions 120, the depressions can be located opposite to each other, FIGS. 3 and 5. In the selected protrusion having three, four, or more depressions 120, the depressions can be spaced substantially equidistantly from one another, as viewed in the cross-section perpendicular to the longitudinal axis B of the selected protrusion (FIGS. 3-5) or can be differentially spaced from one another (not shown). In the embodiments shown in FIGS. 3-5, the depressions 120 extend through the entire length of the selected protrusion. In other embodiments, the depression or depressions 120 can extend only through a portion of the selected protrusion, as shown, for example, in FIG. 7. The depression can extend from the base of the selected protrusion and terminate before it reaches the free end of the selected protrusion; or the depression can extend from the free end of the selected protrusion and terminate before it reaches the base of the selected protrusion. The embodiment may be contemplated in which the selected protrusion has more than one depression wherein at least one depression extends through the entire length of the protrusion, and the other depression or depressions extends only through a portion of the length of the protrusion in any manner described herein above.

The protrusions 50 may have differential lengths. In one embodiment, for example, the lengths of the protrusions 50 may be such that the ends of several protrusions consecutively disposed next to one another, as viewed in a cross-section of the brush perpendicular to the major axis A, form an imaginary line that is straight (FIG. 3, line 60). In another embodiment, such a line can be concave (not shown) or convex (FIG. 3, line 70). Thus, in its cross-section perpendicular to the major axis A, the brush may or may not be circumferentially symmetrical.

The protrusions 50 can be made to gradually taper from the base towards the free end (FIGS. 1-6). Alternatively, the protrusions 50 may have a generally uniform thickness (with the exception of the selected protrusions, cross-sections of which are at least partially affected by the longitudinal depression), or taper from the free ends towards the bases of the protrusions 50 (not shown).

Figure 4:
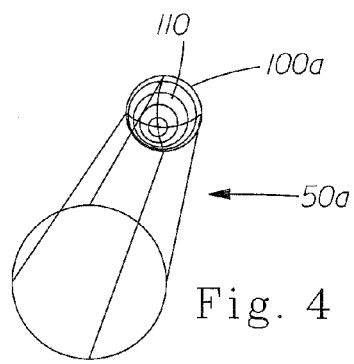

In one embodiment, the ends of at least some of the protrusions 50 may have concave depression 110, FIG. 4. Those concave depressions 110 are different and distinct from the depressions 120 in the walls of the protrusions, for the depressions 110 in the free ends of the protrusions 50 are not disposed longitudinally in relation to the longitudinal axes B of the protrusions 50. In some embodiments of the brush of the present invention, the selected protrusions can have both the longitudinal depression or depressions 120 and the concave depression 110 at the free end of the selected protrusion.

The longitudinal axes B of the protrusions 50 and the major axis A of the brush 10 can be mutually perpendicular. The embodiment may be contemplated when they are not mutually perpendicular, i.e., the axes B of at least some of the protrusions 50 and the major axis A of the brush 10 may form acute angles, obtuse angles, angles there between, and mixtures thereof, FIGS. 12 to 15.

The brush of the present invention can be made by using a variety of techniques known in the art such as assembly of stacked disks, Stereolithography (SL) of suitable resins, or single/multiple part "injection molding." Particularly, injection molding is, in essence, a process wherein molten plastic is deposited under pressure, or injected, into a closed form having a cavity of a desired shape, to fill the cavity, then cooled to solidify in the cavity, and then released from the cavity. One skilled in the art will appreciate that using the injection molding process, it is possible to form virtually any desired configuration of the protrusions, including the selected protrusions of the present invention. In addition, the injection molding technique allows one to control the length of individual protrusions, so that trimming of the finished brush may not be needed in order to form a certain cross-sectional profile of the brush, as shown, for example, in FIG. 2.

Figure 8:
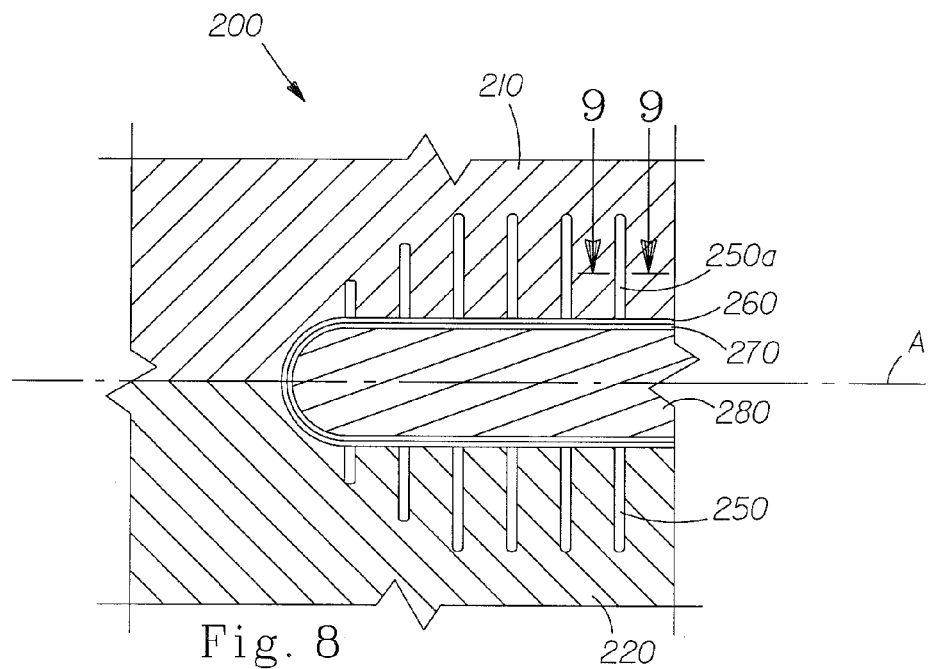
FIG. 8 is a schematic cross-sectional view of an embodiment of a support form that can be used for making the brush of the present invention by injection molding.
Figure 9:
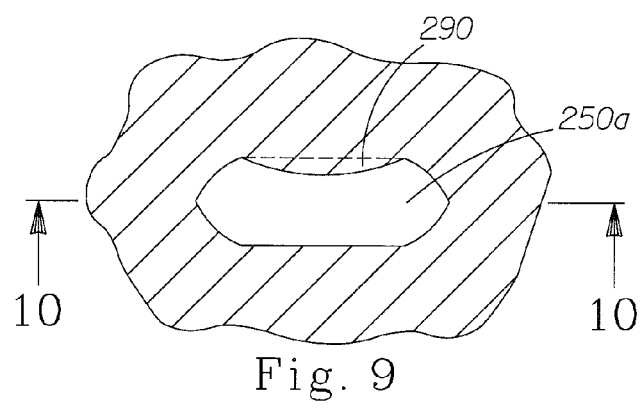
FIG. 9 is a schematic cross-sectional and partial view of the form shown in FIG. 8, taken along lines 9-9, and showing a cross-section of a selected protrusion-forming channel having a protuberance therein.
Figure 10:
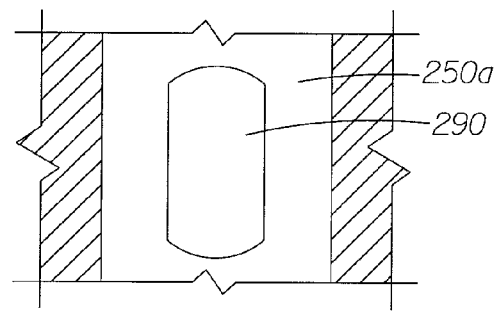
FIG. 10 is a schematic cross-sectional view taken along lines 10-10 of FIG. 9, and showing a plan view of one embodiment of the protuberance of the protrusion-forming channel.

The brush of the present invention can be made by an injection-molding process, for example using a multi-component molding injection machine 200, schematically shown in FIG. 8. First, a hollow stem 260 is provided. The hollow stem 260 can be made from any suitable material, for example, plastic or resin such as polypropylene, and may include any suitable thermoplastic or thermosetting materials. The hollow stem 260 can be formed by injection-molding or any other means known in the art. As an example, in FIG. 8, the hollow stem 260 is formed and disposed in the injection machine 200. The hollow stem 260 may comprise any suitable shape in its cross-section perpendicular to the major axis, for example, cylindrical (shown in the exemplary embodiment of FIG. 1), rectangular, triangular, circular, polygonal, or any combination thereof, or any other shape, including irregular geometric shape (not shown).

Figure 11:
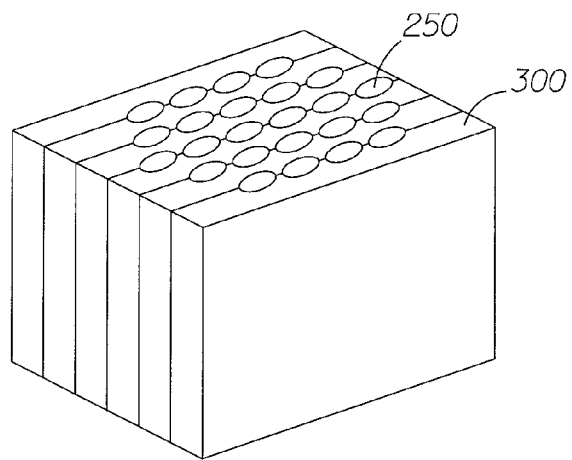
FIG. 11 is a schematic perspective view of one embodiment of the protrusion-forming channels.
Figure 12:
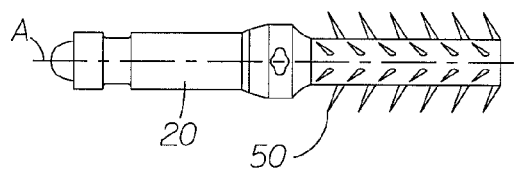
FIGS. 12 to 13 is a side view of an embodiment of a brush according to the invention showing a mixture of obtuse and acutely angled protrusions.
Figure 13:
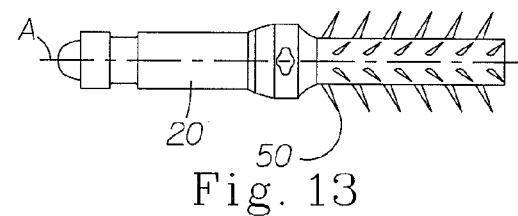
Figure 14:
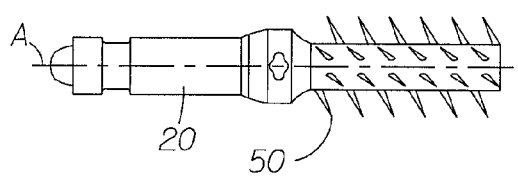
FIG. 14 is a side view of an embodiment of a brush according to the invention showing the protrusions at obtuse angles.
Figure 15:
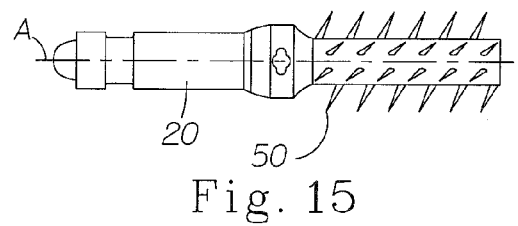
FIG. 15 is a side view of an embodiment of a brush according to the invention showing the protrusions at acute angles.

A plurality of protrusion-forming channels 250 is provided. The protrusion-forming channels 250 are disposed so that their entrances abut the hollow stem 260 in predetermined locations in which the protrusions 50 of the brush being constructed should be disposed after the brush has been constructed. The overall configuration and geometry of the protrusion-forming channels 250 corresponds to the desired overall geometry and configuration of the brush being made. Each of the protrusion-forming channels 250 terminates with an end and has a predetermined length. Depending on the size and length of the protrusion-forming channels 250, the protrusion-forming channels 250 can be made by any means known in the art, for example using conventional drilling techniques, laser, chemical erosion, wire electrical discharge machine (EDM), or any other suitable means. The protrusion-forming channels 250 can be formed, for example, by a plurality of coated plates 300 (FIG. 11) disposed consecutively adjacent to one another, wherein mutually adjacent plates 300 have surface patterns that form, in combination, a desired profile of the protrusion-forming channels 250.

In accordance with the present invention, the plurality of protrusion-forming channels 250 may include selected protrusion-forming channels 250a, i.e., the channels that are structured to form the selected protrusions having at least one external depression 120 thereon, as described herein above. For this purpose, each of the selected protrusion-forming channels 250a has at least one protuberance 290 therein. The protuberance or protuberances 290 can be disposed along the length of the selected protrusion-forming channel 250a, at the end of the selected protrusion-forming channels 250a, or both, depending on a desired configuration of the selected protrusion being formed.

In the next step, a second moldable material 270 is injected, under pressure, into the hollow stem, to form the protrusions (FIG. 8). The second moldable material can comprise the material identical to the first moldable material, or, alternatively, may differ therefrom. Only for the purposes for example, the second moldable material can comprise any suitable thermoplastic elastomer (TPE), such as, for example, styrene-ethylene-butylene-styrene (SEBS) block copolymer. The pressure under which the second moldable material 270 is injected should be sufficient to rapture the hollow stem 260 and form perforations in locations corresponding to the protrusion-forming channels 250 and further to fully fill the protrusion-forming channels 250 with the second moldable material 270 so that the second moldable material 270 assumes the shape of the protrusion-forming channels 250. These perforations formed in the stem 260 serve, in effect, as spinnerets for the second moldable material. The second moldable material 270 that fills, under pressure, the selected protrusion-forming channels 250 forms the selected protrusions that have external depressions described herein above, the depressions being a "negative" of the protuberances 290 of the selected protrusion-forming channels 250a.

After the second moldable material 270 solidifies in the protrusion-forming channels 250, the brush comprising the stem 260 and the plurality of protrusions 50 extending therefrom can be released from the injection machine. If the plurality of plates 300 is used to form the protrusion-forming channels 250, the plates 300 can be moved apart from one another, thereby releasing the formed protrusions 50.

If desired, an optional step of injecting a third moldable material 280 (FIG. 8) into the hollow stem 260 to fill the stem 260, can be used. When the process is completed, the protrusions 50 are integrally bound to the third material 280 that has filled the stem 260. The third moldable material can comprise a material identical to at least one of the first moldable material or the second moldable material, or can be chosen to be different from either the first moldable material or the second moldable material.

B. Composition

Compositions of the present invention are formulated such that when combined with the applicator brush disclosed herein, will deposit a thick coating of large particles, designated "primary particles" or a cosmetic composition comprising the same onto keratinous fibers. In the case of mascara compositions, such a formulation will help to improve volume of lashes.

Preferably, compositions of the present invention have a yield point of from about 0 Pa to about 1000 Pa, more preferably from about 25 Pa to about 500 Pa, still more preferably from about 35 Pa to about 200 Pa. Preferably, compositions of the present invention have a viscosity of from about 2000 centipoise to about 6000 centipoise at 25° C. at a 200s^-1 shear rate, more preferably from about 2500 centipoise to about 5000 centipoise, still more preferably from about 3000 centipoise to about 4500 centipoise.

Primary or secondary particles of the present invention may be produced from inorganic or organic material that is non-irritating and nontoxic for use on keratinous fiber. The primary particles are considered large since they are found in the present invention to be above about 5 microns in equivalent diameter. Particles of the present invention are measured by their "equivalent diameter" wherein "equivalent diameter" includes the diameter of a circular particle or the diameter of the circle in which the cross-section of a non-circular particle is inscribed. There are particles, however, of the present invention that are considered primary particles even if they may initially be less than 5 microns in equivalent diameter. Because some particles may increase their size after application to keratinous fiber, primary particles suitable for the present invention may also comprise those particles that are initially less than 5 microns equivalent diameter but swell to a size greater than 5 microns in equivalent diameter by any chemical or physical means. For example, if a mascara composition is used, particles that are initially less than about 5 microns in equivalent diameter may be used but at some point after the particles are deposited onto the lashes, the particles are swelled to a size suitable for the present invention which is no less than about 5 microns, no less than about 10 microns, or no less than about 15 microns and no more than about 100 microns, no more than about 75 microns, or no more than about 50 microns in equivalent diameter. Therefore, "primary particles that are at least about 5 microns" includes primary particles that are initially at least about 5 microns in equivalent diameter or primary particles that have increased to a size of at least about 5 microns in equivalent diameter by any chemical or physical means. Such dimensions will enable a mascara film of about 5 to about 100 microns in equivalent diameter to deposit onto the lash which will provide the user with an impression of noticeable lashes.

The molded applicator disclosed herein is designed to transfer particles of this magnitude from the holding vessel to the lash without filtering out or losing the particles. Such applicator will also sufficiently comb or separate the lashes to achieve the desired look.

The primary particle types of the composition may be solid, hollow, or porous. When the particles employed in accordance with the present invention are porous particles, their range corresponds, for example, to a surface area of at least about 0.25 m2/g, at least about 0.5 m2/g, or at least about 1 m2/g. For example, microporous particles sold by Dow Corning under the trade name Polytrap Q5-6603® or those sold by LCW under the trade name Covabead LH 170® which is about 9 microns in diameter and about 170 m²/g surface area are examples of porous particles. Primary particles of the present invention may also be hydrophilic or hydrophobic. They may also be spherical, oval, ovoid, platelet, star, rod, cubic or irregularly shaped. As used herein, "irregularly shaped" is considered to be any shape that is not included as spherical, oval, ovoid, platelet, star, rod or cubic. In order to build film thickness as the primary benefit on keratinous surfaces, the dimensions of the particles useful in the present invention should be at least about 1 micron. "Dimension", as used herein, include, but is not limited to height, width, length, and diameter. This is intended to ensure that particles of the present invention rise above the keratinous substrate at least 5 microns in equivalent diameter. In the case of mascara compositions, platelets tend to be too thin and do not stack efficiently to create a thick coating of mascara on the lash. Therefore, for mascara compositions of the present invention, flat platelets as a primary particle, while possible and useful, are a shape less desired.

The primary particles may be composed primarily of a wax or a combination of waxes. In mascara compositions, waxes are typically from about 0% to about 40% as a hydrophobic material that will add bulkiness to the mascara coating and hold the curl of the lashes in place. While these waxes are typically emulsified or dispersed into the carrier vehicle, their "particulate" nature readily breaks down when the mascara is applied from aggregated wax particles to much smaller (typically less than 5 microns in equivalent diameter and often indistinguishable as a particle since they form a more continuous film) and typically platelet-shaped sheets of wax that interlock together to form a relatively smooth film on the lash. Large wax particles, however, between about 5 microns to about 2000 microns in equivalent diameter can be preformed, before addition to the mascara formulation, using processes known in the art such as spray drying and fluidized bed processing. These processes atomize liquid wax and the droplets of wax quickly cool and solidify to create a small, discrete wax particle. The melting point of the particle must be sufficiently high and the particle must be introduced into the mascara formulation at a sufficiently low temperature that it does not soften due to temperature or interactions with other materials in the formulation. The wax particle is intended to retain at least some to most of its size and shape by visual observation during addition into the composition and during application to keratinous fiber such that it maintains its bulkiness even after being applied to the keratinous fiber.

The wax particle may contain other material embedded inside of it. This is achieved by mixing other materials with the molten wax before it is atomized and cooled to create a solid wax particle. Example of materials that can be embedded inside the wax particles include, but are not limited to pigments, preservatives, fillers, active ingredients, polymers, organic and inorganic solids, and mixtures thereof.

Waxes are defined as lipophilic fatty substances, which are solid at room temperature (25 C), that undergo a reversible solid-liquid change of state, with a melting point of greater than or equal to about 30° C., and up to about 150° C., and have an anisotropic crystal organization in solid form. For example, the waxes that may be suitable for this composition may have a melting point of greater than about 40° C., greater than about 50° C., or greater than about 55° C. Waxes may be selected from the group consisting of animal waxes, vegetable waxes, mineral waxes, synthetic waxes and mixtures thereof.

The specific waxes useful in the present invention may be selected from the group consisting of beeswax, lanolin wax, shellac wax (animal waxes); carnauba, candelilla, bayberry (vegetable waxes); ozokerite, ceresin (mineral waxes); paraffin, microcrystalline waxes (petroleum waxes); polyethylene (ethylenic polymers); polyethylene homopolymers (Fischer-Tropsch waxes); C24-45 alkyl methicones (silicone waxes), insect wax, bayberry, spermaceti wax, mountain wax, rice bran wax, kapok wax, haze wax, jojoba wax, rice wax, cotton wax, Japan Wax; and mixtures thereof. Non-limiting mention may also be made of the waxes obtained by catalytic hydrogenation of oils chosen from animal, plant, and synthetic origins comprising at least one fatty chain chosen from linear and branched C8-C32 fatty acids, for example hydrogenated jojoba oil, hydrogenated sunflower oil, hydrogenated caster oil, hydrogenated coconut oil, and hydrogenated lanolin oil, bis(1,1,1-trimethylolpropane)tetrastearate sold under the name Hest 2T-4B by the company Heterene. Non-limiting mention can also be made of silicone waxes and fluoro waxes, and mixtures thereof.

The primary particles may also be hollow in nature. They may be hollow such as those that possess an external shell and at least one single closed cavity. Examples of materials that form an external shell for the hollow particle include homopolymers or copolymers composed of one or more types of monomer selected from vinyl chloride, vinyl acetate, methyl vinyl ether and other vinyl based monomers, acrylic acid, acrylic acid ester, methacrylic acid, methacrylic acid ester, acrylonitrile, methacrylonitrile and other acrylic monomers, styrene, vinylidene chloride, divinylbenzene and ethylene glycol dimethacrylate. For example, materials such as copolymers composed of two or more types of monomer selected from acrylic acid, methacrylic acid or esters thereof, vinylidene chloride, acrylonitrile and methacrylonitrile may be used. These polymers can be produced by crosslinking with a crosslinking agent such as divinylbenzene, ethylene glycol dimethacrylate and triacrylformal. The hollow particle may contain a volatile agent, such as a hydrocarbon (for example, isobutene) and can be prepared in accordance with known procedures, for example those described in U.S. Pat. No. 3,615,972 and in EP patent application 0056219. There are no particular restrictions on volatile agents, and examples include methane, ethane, propane, butane, isobutane, isobutene, pentane, isopentane, neopentane, hexane, neohexane, heptane, acetylene and other hydrocarbons, trichlorofluoromethane, dichlorodifluoromethane and other halogenated hydrocarbons and tetraalkylsilanes and other low boiling compounds.

Primary particles of the present invention may have a specific gravity of at least about 0.02. For example, hollow particles are generally commercially available such as the Matsumoto F-E series, which includes particles such as the water dispersion product F-30E which is about 30-60 microns in diameter and about 0.02-0.03 specific gravity. Akzo Nobel also sells hollow spheres such as 551DE20d70, which is about a 15-25 micron hollow sphere with a specific gravity of about 0.07+/−0.006, or Expancel® 551DE80d42, which is about a 50-80 micron hollow sphere with a specific gravity of about 0.042+/−0.004. Ganz Chemical Company also supplies hollow spheres with a particle diameter of about 8 microns. Hollow inorganic particles are formed from inorganic material such as glass encapsulating a volatile foaming agent that is gasified when heated and is produced by heating this material to swell or foam it. Alternatively, hollow inorganic powder is fly ash generated in a process in which carbon (micropowder carbon) is incinerated. Hollow inorganic particles are commercially available and examples include 3M's Microsphere products which include S60HS with a specific gravity of about 0.6 and an average particle diameter of about 30 microns or K46 with a specific gravity of about 0.46 and an average particle size of about 40 microns.

The particles may be comprised of one or more materials which are polymeric in nature selected from the group consisting of thermoplastic and thermoset polymer particles. The polymers which can be used in the context of the present invention may have a molecular weight of from about 2000 to about 25,000,000. When a thermoplastic polymer particle is used, the Tg may be no less than about −150° C., specifically no less than about −130° C., and no more than about 300° C., specifically no more than about 200° C. The polymer can be combined with a plasticizer to adjust the properties of the polymer. As used herein, the term "plasticizer" refers to a material applied to a given film-forming polymer to soften or improve its flexibility. In the case of a mascara composition, a plasticizer may help the particle to partially deform when applied to lashes, creating a smoother, more flexible mascara film.

The polymeric particles of the present invention will preferably retain much of their shape and bulkiness once they are applied to the keratinous fiber. For example, polymeric particles of the present invention may be those such as Expancel® particles, which are hard and undeformable polymeric particles. Other polymeric particles of the present invention may be, for example, malleable particles whose shape may partially deform when applied to the lashes so as to allow for a smoother thick coating of composition. Polymeric particles of the present invention, for example, may comprise a high molecular weight dimethicone such as Dow Corning's HMW2220 or Dow Corning's 5-7137 dimethicone particle emulsions.

Optionally, compositions of the present invention may comprise additional particles, as used herein "secondary particles", to provide other benefits such as preservation, opacity, coating smoothness, color, transfer resistance, rheological modification, lash separation, or combinations thereof. For example, the composition may comprise pigment particles such as iron oxides which may be used to create a variety of colors including, but not limited to, black mascara film. Other examples include, but are not limited to, latex particles which may be used to impart transfer resistance to the mascara; 25 micron in equivalent diameter platelets which may be combined with 20 micron in equivalent diameter spherical primary particles to create a smoother mascara film; and 5 micron in equivalent diameter spherical particles which could be used to fill in void space between 40 micron in equivalent diameter primary particles to impart a smoother mascara film.

Coatings on Particles

In addition, the surfaces of the primary or secondary particles may be coated with either chemical matter, particulates, or a combination of both. There are no particular restrictions on the materials that may be applied to the surface of the particle, and materials may be selected in accordance with the intended effect. Examples of particulate-type coatings include, but are not limited to talc, sericite, mica, calcium carbonate, magnesium carbonate, kaolin, boron nitride, titanium oxide, zinc oxide, iron oxide, cerium oxide, zirconium oxide and silica. Relevant examples include the MFL series of particles from Matsumoto. The 30STI material has a coating of TiO2 on a 20 micron sphere with a composite specific gravity of about 0.2+/−0.05. The 60CA material, also from Matsumoto has a coating of calcium carbonate on a 40-60 micron particle with a composite specific gravity of about 0.13+/−0.05. Examples of chemical-based coatings include, but are not limited to lecithin, silicones, hydrocarbons, fluorinated silicones, fluorinated hydrocarbons, organic and inorganic polymeric compounds, and amphiphilic materials. These treatments may be physical coatings or covalently bound to the particle surface.

Volume Fraction of Particles

When used as a single-step, single formula composition, the volume fraction of the particles is considered to be the ratio of the total combined volume of particles in the composition to the total volume of the composition prior to drying on the keratinous fibers. The ratio of particles to total composition may be, for example, about 1:20 to about 10:1, further, for example, about 1:15 to about 5:1 and further, for example, about 1:12 to about 3:1. Moreover, when used as part of a multiple step cosmetic system comprising a pure particle composition, i.e. 100% particles and absent a carrier, the particles may be applied as an additional layer wherein the particles are applied to the lashes as a second application step after the initial composition of the present invention has been applied. When such a complimentary composition is used, the composition may comprise 100% particles, 95% particles, 85% particles or 75% particles by total combined volume of particles within the composition. The remainder of the composition may comprise a binder, for example, an oil that aids in holding the particles together within the composition.

Dermatologically Acceptable Carrier

Compositions of the present invention may contain a dermatologically acceptable carrier. The carrier can be volatile or nonvolatile. Suitable carriers are those that dissolve or uniformly disperse the particles of the present invention. They include, but are not limited to, water, lower alcohols (such as ethanol, isopropanol), dihydric alcohols such as propylene and butylene glycol, polyols such as glycerin, hydroalcoholic mixtures, hydrocarbons (such as isobutane, hexane, decene, acetone, isododecane, and straight or branch chained hydrocarbons having about 8 to about 20 carbon atoms), halogenated hydrocarbons (like Freon), linalool, hydrocarbon esters (such as ethyl acetate, dibutyl phthalate), volatile fluids, phenethyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane), volatile dimethicone, and mixtures thereof.

C. Optional Ingredients

The compositions of the present invention may contain numerous optional ingredients that may be added to provide additional benefits in addition to the benefits already mentioned. For example, compositions of the present invention may contain a preservative system to inhibit microbiological growth and maintain the integrity of the product. In the present invention, the preservative system does not have a detrimental effect on the composition. Optional ingredients should be suitable for application to mammalian skin, that is, when incorporated into the compositions they are suitable for use in contact with human skin without undue toxicity, incompatibility, instability, allergic response, and the like, within the scope of sound medical or formulator's judgment. The *CTFA Cosmetic Ingredient Dictionary & Handbook*, Tenth Edition (2004) describes a wide variety of nonlimiting cosmetic and pharmaceutical ingredients commonly used in the skin care industry, which are suitable for use in the compositions of the present invention.

Any optional ingredients known to those skilled in the art may also be used in the invention. Examples of optional ingredients are cosmetic fillers including, but not limited to, mica, talc, nylon, polyethylene, silica, polymethacrylate, kaolin, and Teflon. Suitable cosmetic preservatives including, but not limited to, methylparaben, propylparaben, butylparaben, ethylparaben, potassium sorbate, trisodium EDTA, phenoxyethanol, ethyl alcohol, benzyl alcohol, diazolidinyl urea, imidazolidinyl urea, and quaternium-15 may also be included.

The optional components useful herein can be categorized by their therapeutic or aesthetic benefit or their postulated mode of action. However, it is to be understood that the optional components useful herein can in some instances provide more than one therapeutic or aesthetic benefit or operate via more than one mode of action. Therefore, classifications herein are made for the sake of convenience and are not intended to limit the component to that particular application or applications listed. Suitable optional ingredients are detailed below.

Film-Forming Polymers

Film-forming polymers may be used in the invention. The expression "film-forming" is understood to refer to a polymer system which allows a film to be formed when it is spread on glass. Film-forming polymers of the present invention may be water-soluble or water-dispersible polymers. Examples of water-soluble polymers include, but are not limited to, polyvinylpyrilidone and polyvinyl alcohol. Examples of water-dispersible polymers are ammonium acrylates copolymer and polyurethane. The film-forming polymers can also be oil soluble. Example of oil soluble film-forming polymers may be, but are not limited to, trimethylsiloxysilicate, dimethicone, and hydrogenated polycyclopentadiene.

Pigments

Particles present in the composition may contain dermatologically-acceptable pigments selected from the group consisting of inorganic pigments, organic pigments, and organic lake pigments, pearlescent pigments, and mixtures thereof. If the particle is a primary particle, the primary particle may be partially pigmented while secondary particles may wholly or partially comprise one or more pigments. When employed, the pigments are present in proportions depending on the color and the intensity of the color that it is intended to produce. The level of pigments in the solid portion of the composition may be from at least about 0.01%, at least about 1%, or at least about 3% but no more than about 20%, no more than about 15%, or no more than about 10%. The pigments may be surface-treated with treatments that include, but are not limited to, silicones, perfluorinated compounds, lecithin, and amino acids.

Inorganic pigments useful in the present invention include those selected from the group consisting of rutile titanium dioxide, anatase titanium dioxide (both coded in the Color Index under the reference CI 77891); black, yellow and red iron oxides (CI 77499, 77492 and 77491); bismuth oxychloride (CI 77163); manganese violet (CI 77742); ultramarines (CI 77007); chromium oxide (CI 77288); chromium hydroxide (CI 77289); ferric ferrocyanide (CI 77510); zinc oxide (CI 77947); and mixtures thereof.

The organic pigments useful in the present invention include the dyes and the analogous lakes selected from the group consisting of D&C Red 6 (CI 15850); D&C Red 7 (CI 15850:1); D&C Red 21 (CI 45380:2); D&C Red 22 (CI 45380); D&C Red 27 (C1-45410:1); D&C Red 28 (CI 45410); D&C Red 30 (CI 73360); D&C Red 33 (CI 17200); D&C Red 34 (CI 15880:1); D&C Red 36 (CI 12085); D&C Orange 4 (CI 15510); D&C Orange 5 (CI 45370:1); D&C Orange 11 (CI 45425); FD&C Yellow 5 (CI 19140), FD&C Yellow 6 (CI 15985); D&C Yellow 10 (CI 47005); FD&C Green 3 (CI 42053); D&C Green 5 (CI 61570); FD&C Blue 1 (CI 42090); Cochineal Carmine (CI 75470); Guanine (CI 75170); carbon black; and mixtures thereof.

The pearlescent pigments useful in the present invention include those selected from the group consisting of mica (or a similar plate-like substrate) coated with any of the following materials alone or in combination: titanium dioxide, bismuth oxychloride, iron oxides, ferric ferrocyanide, chromium oxide, chromium hydroxide, and any organic pigment of the above-mentioned type and mixtures thereof.

Emulsifiers

Emulsifiers may also be used to assist in the stabilization of the compositions. These emulsifiers include, but, are not necessarily limited to soaps, phosphate esters, ethoxylated alcohols, ethoxylated fatty acids, ethoxylated fatty esters, polyol ether esters, glycerol esters, sucrose or sorbitan esters, glucose esters, potassium or DEA-cetyl phosphate, triethanolamine, fatty esters, and mixtures thereof.

Rheological Agent

One or more rheological agents may be used to alter the rheology of the mascara. For example, they may be shear-thinning thickeners, i.e., an agent capable of giving the composition containing it shear-thinning behavior, characterized in that the viscosity of the composition decreases when increased shear rates are applied to the composition.

Hydrophobic Conditioning Agents

The compositions of the present invention may optionally contain one or more hydrophobic conditioning agents. For example, the weighted arithmetic mean solubility parameter of the hydrophobic conditioning agent may be less than or equal to 12. It is recognized, based on this mathematical definition of solubility parameters, that it is possible, for example, to achieve the required weighted arithmetic mean solubility parameter, i.e., less than or equal to 12, for a hydrophobic conditioning agent comprising two or more compounds If one of the compounds has an individual solubility parameter greater than 12.

Solubility parameters are well known to the formulation chemist of ordinary skill in the art and are routinely used as a guide for determining compatibilities and solubilities of materials in the formulation process.

Nonlimiting examples of hydrophobic conditioning agents include those selected from the group consisting of mineral oil, petrolatum, lecithin, hydrogenated lecithin, lanolin, lanolin derivatives, C7-C40 branched chain hydrocarbons, C1-C30 alcohol esters of C1-C30 carboxylic acids, C1-C30 alcohol esters of C2-C30 dicarboxylic acids, monoglycerides of C1-C30 carboxylic acids, diglycerides of C1-C30 carboxylic acids, triglycerides of C1-C30 carboxylic acids, ethylene glycol monoesters of C1-C30 carboxylic acids, ethylene glycol diesters of C1-C30 carboxylic acids, propylene glycol monoesters of C1-C30 carboxylic acids, propylene glycol diesters of C1-C30 carboxylic acids, C1-C30 carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol C4-C20 alkyl ethers, di C8-C30 alkyl ethers, straight and branched chain hydrocarbons having from about 7 to about 40 carbon atoms and combinations thereof.

Other hydrophobic conditioning agents include, but are not limited to, hydrophobic chelating agents; C1-C30 alcohol esters of C1-C30 carboxylic acids and of C2-C30 dicarboxylic acids; various C1-C30 monoesters and polyesters of sugars and related materials; Nonvolatile silicones such as polydialkylsiloxanes, polydiarylsiloxanes, and polyalkarylsiloxanes; Vegetable oils and hydrogenated vegetable oils; and C4-C20 alkyl ethers of polypropylene glycols, C1-C20 carboxylic acid esters of polypropylene glycols, and di-C8-C30 alkyl ethers.

Hydrophilic Conditioning Agents

The compositions of the present invention can also include one or more hydrophilic conditioning agents. Nonlimiting examples of hydrophilic conditioning agents include those selected from the group consisting of polyhydric alcohols, polypropylene glycols, polyethylene glycols, ureas, pyrolidone carboxylic acids, ethoxylated and/or propoxylated C3-C6 diols and triols, alpha-hydroxy C2-C6 carboxylic acids, ethoxylated and/or propoxylated sugars, polyacrylic acid copolymers, sugars having up to about 12 carbons atoms, sugar alcohols having up to about 12 carbon atoms, and mixtures thereof.

Structured Conditioning Agents

Compositions of the present invention may also include structured conditioning agents. Suitable structured conditioning agents include, but are not limited to, vesicular structures such as ceramides, liposomes, and the like.

Coacervates

Compositions of the present invention may also include cosmetic agents that are coacervate-forming. For example, the coacervate-forming cosmetic benefit agent comprises a cationic polymer, an anionic surfactant, and a dermatologically acceptable carrier for the polymer and surfactant. The cationic polymer may be selected from the group consisting of natural backbone quaternary ammonium polymers, synthetic backbone quaternary ammonium polymers, natural backbone amphoteric type polymers, synthetic backbone amphoteric type polymers, and combinations thereof.

Vitamin Compounds

The present compositions may comprise vitamin compounds, precursors, and derivatives thereof. These vitamin compounds may be in either natural or synthetic form. Suitable vitamin compounds include, but are not limited to, Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, etc.), and Vitamin K (e.g., phytonadione, menadione, phthiocol, etc.) compounds.

Preservatives

Suitable cosmetic preservatives including, but not limited to, methylparaben, propylparaben, butylparaben, ethylparaben, potassium sorbate, trisodium EDTA, phenoxyethanol, ethyl alcohol, benzyl alcohol, diazolidinyl urea, imidazolidinyl urea, and quaternium-I 5 may also be included.

Waxes

If waxes are used as an optional component of the present invention, the waxes are not considered a primary particle, but rather particles that are less than about 5 microns in diameter. In such case, the particle size is considered after the particles have been applied to the lashes in order to account for the diminution upon application. Optional waxes may be used at levels from about 0%, from about 2% or from about 5% but no more than about 20%, no more than about 30% or no more than about 40% by weight of the composition. Waxes are defined as lipophilic fatty substances, which are solid at room temperature (25° C.), that undergoes a reversible solid-liquid change of state, with a melting point of greater than or equal to about 30° C., and up to about 150° C., and have an anisotropic crystal organization in solid form. For example, the waxes that may be suitable for this composition may have a melting point of greater than about 40° C. or greater than about 50° C. Waxes useful in the present invention may be selected from the group consisting of animal waxes, vegetable waxes, mineral waxes, synthetic waxes and mixtures thereof.

The specific waxes useful in the present invention as optional ingredients may be selected from the group consisting of beeswax, lanolin wax, shellac wax (animal waxes); carnauba, candelilla, bayberry (vegetable waxes); ozokerite, ceresin, (mineral waxes); paraffin, microcrystalline waxes (petroleum waxes); polyethylene, (ethylenic polymers); polyethylene homopolymers (Fischer-Tropsch waxes); C24-45 alkyl methicones (silicone waxes), Chinese insect waxes, rice wax, Japan Wax; and mixtures thereof. Most preferred are beeswax, lanolin wax, carnauba, candelilla, ozokerite, ceresin, paraffins, microcrystalline waxes, polyethylene, C24-45 alkyl methicones, and mixtures thereof. Non-limiting mention may also be made of the waxes obtained by catalytic hydrogenation of oils chosen from animal, plant, and synthetic origins comprising at least one fatty chain chosen from linear and branched C8-C32 fatty acids, for example hydrogenated jojoba oil, hydrogenated sunflower oil, hydrogenated caster oil, hydrogenated coconut oil, and hydrogenated lanolin oil, bis(1,1,1-trimethylolpropane) tetrastearate sold under the name Hest 2T-4B by the company Heterene. Non-limiting mention can also be made of silicone waxes and fluoro waxes, and mixtures thereof.

Fibers

The secondary particles may also comprise fibers to allow for the improvement of either mascara volume or lengthening of lashes. The term "fiber", as used herein, means an object of length L and diameter D such that L is greater than D, wherein D is the diameter of the circle in which the cross section of the fiber is inscribed. For example, the ratio L/D (or shape factor) may be from at least about 3.5:1 or from about 5:1 but no more than about 500:1 or no more than about 150:1. The fibers that may be used in the composition may be chosen from mineral and organic fibers of synthetic or natural origin. For example, they be short or long, individual or organized, such as being braided, and hollow or solid. They may have any shape, such as a circular or polygonal (square, hexagonal, or octagonal) cross section, depending on the intended specific application. For example, their ends may be blunt and/or polished to prevent injury. For example, the fibers may have a length ranging from at least about 1 micron, at least about 50 microns or at least about 90 microns but no more than about 100 microns, no more than about 5 mm, or no more than about 1 mm. The weight or yarn count of the fibers may be given in units of denier or decitex, and may represent the weight in grams per 9 km of yarn. In one embodiment, the fibers may have a yarn count from at least about 0.15 or from at least about 0.18 but no more than about 30 denier or no more than about 18 denier.

The fibers of the present invention may be treated or untreated at the surface, and coated or uncoated. If coated fibers are used, non-limiting mention may be made of polyamide fibers coated with copper sulphide, which may provide an anti-static effect (for example R-STAT from Rhodia), or another polymer which may enable a particular organization of the fibers (specific surface treatment), or surface treatment, such as color/hologram effects (Lurex fiber from Sildorex, for example).

The composition may also comprise "rigid" fibers which are initially substantially straight, when placed in a dispersing medium, do not undergo a substantial change in shape, reflecting a shape that may be described as still substantially straight and linear. The rigid fibers may be chosen from fibers of a synthetic polymer chosen from polyesters, polyurethanes, acrylic polymers, polyolefins, polyamides, such as non-aromatic polyamides, and aromatic polyimideamides.

For example, the rigid fibers may be chosen from aromatic polyimideamide fibers. Further for example, polyimideamide yarns or fibers that may be used for the compositions of the invention are described, for example, in the document from R. Pigeon and P. Allard, Chimie Macromo-lCculaire AppliquCe, 40141 (1974), pages 139-158 (No. 600), or in U.S. Pat. No. 3,802,841, or in documents FR-A-2 079 785, EP-A1-0 360 728 and EP-A-0 549 494.

Example 1

Oil-in-Water Mascara Composition

A mascara containing large wax particles:

| Phase | Raw Material | Weight % |
|---|---|---|
| A | Glyceryl Monostearate | 5.250 |
| A | Black Iron Oxide | 7.250 |
| A | Disteardimonium Hectorite | 2.250 |
| A | Stearic Acid | 2.750 |
| A | Carnauba Wax | 2.000 |
| A | Triethanolamine | 1.750 |
| A | Synthetic Wax | 1.500 |
| A | Polyvinyl Alcohol | 1.500 |
| A | Propylene Carbonate | 0.750 |
| A | Lecithin | 1.250 |
| A | Oleic Acid 80% | 1.000 |
| B | Acrylates Copolymer | 5.170 |
| B | Deionized Water | 40.18 |
| B | Simethicone Emulsion 30% | 0.200 |
| C | Xanthan Gum | 0.6 |
| C | Propylene Glycol | 3.000 |
| D | Ammonium Acrylates Copolymer | 17.79 |
| E | Ethyl Alcohol SD 40-B | 1.000 |
| E | Benzyl Alcohol | 0.650 |
| E | Panthenol | 0.280 |
| E | Phenoxyethanol | 0.280 |
| E | Methylparaben | 0.200 |
| E | Ethylparaben | 0.200 |
| E | Propylparaben | 0.100 |
| E | Trisodium EDTA | 0.100 |
| F | 20 μm Polyethylene Wax Particle | 3.000 |
| | TOTAL | 100.000 |

Procedure

Phase A is heated to melt the waxes and allow the pigment to be dispersed with a Cowles Blade mixer. Phase B materials are stirred together at ambient conditions, and Phase C materials are stirred together at ambient conditions and then it is added to Phase B (to gel Phase B), and the mixture is stirred and then heated to about 85 C. The Phase A and Phases B/C are mixed together to create an oil (wax) in water emulsion. The mixture is stirred for 15 minutes and then is cooled gradually till room temperature. During the cool down, Phases D and E are added to the mixture and stirred in below 60 C. Phase F is spherical polyethylene wax particles that are prepared separately using typical process known in the art such as spray drying. Phase F is added to and mixed with the mascara once the mascara has cooled down to about 25 C.

Example 2

Oil-in-Water Mascara Composition

A mascara containing large hollow particles:

| Phase | Raw Material | Weight % |
|---|---|---|
| A | Glyceryl Monostearate | 5.250 |
| A | Black Iron Oxide | 7.250 |
| A | Disteardimonium Hectorite | 2.250 |
| A | Stearic Acid | 2.750 |
| A | Carnauba Wax | 2.000 |
| A | Triethanolamine | 1.750 |
| A | Synthetic Wax | 1.500 |
| A | Polyvinyl Alcohol | 1.500 |
| A | Propylene Carbonate | 0.750 |
| A | Lecithin | 1.250 |
| A | Oleic Acid 80% | 1.000 |
| B | Acrylates Copolymer | 5.170 |
| B | Deionized Water | 41.93 |
| B | Simethicone Emulsion 30% | 0.200 |
| C | Xanthan Gum | 0.6 |
| C | Propylene Glycol | 3.000 |
| D | Ammonium Acrylates Copolymer | 17.79 |
| E | Ethyl Alcohol SD 40-B | 1.000 |
| E | Benzyl Alcohol | 0.650 |
| E | Panthenol | 0.280 |
| E | Phenoxyethanol | 0.280 |
| E | Methylparaben | 0.200 |
| E | Ethylparaben | 0.200 |
| E | Propylparaben | 0.100 |
| E | Trisodium EDTA | 0.100 |
| F | Expancel ® DE40d60 | 1 |
| | Expancel ® DE20d70 | 0.25 |
| | TOTAL | 100.000 |

Procedure

Phase A is heated to melt the waxes and allow the pigment to be dispersed with a Cowles Blade mixer. Phase B materials are stirred together at ambient conditions, and Phase C materials are stirred together at ambient conditions and then it is added to Phase B (to gel Phase B), and the mixture is stirred and then heated to about 85 C. The Phase A and Phases B/C are mixed together to create an oil (wax) in water emulsion. The mixture is stirred for 15 minutes and then is cooled gradually till room temperature. During the cool down, Phases D and E are added to the mixture and stirred in below 60 C. Phase F is spherical hollow particles that are 40 μm and 20 μm average diameters. Phase F is added to and mixed with the mascara once the mascara has cooled down to about 25 C.

Example 3

Oil-in-Water Mascara Composition

A mascara containing large polymeric particles:

| Phase | Raw Material | Weight % |
|---|---|---|
| A | Glyceryl Monostearate | 7.500 |
| A | Black Iron Oxide | 6.500 |
| A | C18-36 Acid Triglyceride | 5.000 |
| A | Stearic Acid | 3.750 |
| A | Carnauba Wax | 2.500 |
| A | Paraffin Wax | 2.500 |
| A | Tricontanyl PVP | 2.000 |
| A | Lecithin | 2.000 |
| A | Potassium Cetyl Phosphate | 1.000 |

-continued

| Phase | Raw Material | Weight % |
|---|---|---|
| A | Triethanolamine | 2.250 |
| B | Trisodium EDTA | 0.100 |
| B | Deionized Water | 34.89 |
| B | Simethicone Emulsion | 0.200 |
| C | Ethyl Alcohol | 1.000 |
| C | Benzyl Alcohol | 0.650 |
| C | Panthenol | 0.280 |
| C | Phenoxyethanol | 0.280 |
| C | Methylparaben | 0.200 |
| C | Ethylparaben | 0.200 |
| C | Propylparaben | 0.100 |
| C | Trisodium EDTA | 0.100 |
| D | Ammonium Acrylates Copolymer | 12.000 |
|   | Dow Corning HMW2220 Dimethicone Emulsion | 15 |
| TOTAL |   | 100.000 |

Procedure

The waxes of Phase A are heated to melt the waxes and then the pigment is added and dispersed into the waxes. Then the Triethanolamine is added and mixed in. Phase B materials are stirred together at ambient conditions, and then heated to the same temperature (~90 C) as Phase A. Phase A and Phase B are combined together and mixed to homogeneity. They are then gradually cooled a 1 C per minute until 50 C when phase C (phase C is premixed together before-hand) is added and mixed in, followed by phase D (premixed beforehand). The mixture is mixed until about 40 C and then allowed to self cool gradually to ambient conditions. During the processes, the Dimethicone emulsion particles (which start as small <5 micron polymer particles) coalesce together to form polymer particles that are greater than 5 microns.

Example 4

Water Based Mascara

A mascara containing platelet particles and hollow particles:

Clear Mascara Master Formula

| Phase | Raw Material | Weight % |
|---|---|---|
| A | Purified Water | 37.00 |
| A | Carbomer | 1.000 |
| B | Polyvinyl Alcohol | 10 |
| B | Purified Water | 28.000 |
| C | Glycerin | 0.500 |
| C | Imidazolidinyl Urea | 0.300 |
| C | Methylparaben | 0.1 |
| C | Trisodium EDTA | 0.050 |
| D | Ethyl Alcohol 200 Proof | 5.000 |
| E | Triethanolamine 99% | 2.200 |
| E | Purified Water | 5.65 |
| F | Particle (Expancel ® DE20d70 from Expancel ®) | 0.200 |
| F | Colorona ® Magenta | 10.000 |
|   |   | 100.000 |

Procedure

The carbomer is gradually added to the Phase A Water and the mixture is stirred. The water in Phase B is heated to about 50° C. and then the rest of phase B is slowly added and stirred in. Add the Phase C materials into the Phase B and continue to mix. Phase A is then added to Phases B/C and mixed in. The batch is cooled to about ambient temperature and then Phase D is added and mixed in. Premix the Phase E materials into a uniform mixture, and add it to the rest of the batch. The viscosity will thicken during this addition. Phase F is gradually added and the batch is stirred to create a homogeneous mixture at ambient conditions.

Example 5

Anhydrous Mascara

A mascara having coated hollow particles:

Product Phasing

| A | Tall Oil Glycerides | 0.500% |
|---|---|---|
| A | Pentaerythrityl Hydrogenated Rosinate | 2.000% |
| A | Carnauba Wax | 5.000% |
| A | Polyethylene Wax | 8.500% |
| A | Trihydroxystearin | 2.500% |
| A | Propylparaben | 0.100% |
| A | BHA | 0.100% |
| A | Phenoxyethanol 99% | 0.800% |
| A | Petroleum Distillates | 63.50% |
| B | Disteardimonium Hectorite | 6.000% |
| C | Propylene Carbonate | 2.000% |
| D | Black Iron Oxide | 7.000% |
| E | Matsumoto MFL 60CA (Calcium Carbonate coated hollow particle) | 2.000% |
|   |   | 100% |

Procedure

Phase A ingredients are melted and mixed together with low shear mixing. Phase B is gradually added to the Phase A and then dispersed with high shear mixing. Phase C is then added and mixed in with high shear mixing. The Phase D is then added and dispersed with high shear mixing. The batch is cooled to ambient conditions and the Phase E is added and mixed in.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the term in a document incorporated herein by reference, the meaning or definition assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A mascara system comprising, in combination:
   (a) a molded, thermoplastic mascara applicator comprising substantially longitudinal stem having a major axis and a plurality of protrusions extending therefrom, wherein at least two adjacent protrusions are spaced from one another at a distance of from about 0.75 mm to about 3.0 mm at the base of the stem; and (b) a mascara composition comprising
  (i) pigment particles,
  (ii) secondary particles, wherein at least some of the secondary particles are fibers having a length of between about 1 micron and about 100 microns and a length to diameter ratio of between about 3.5:1 and about 500:1, and
  (iii) a dermatologically acceptable carrier.

2. The mascara system of claim 1, wherein at least some of the pigments particles are selected from group consisting of inorganic pigments, organic pigments, organic lake pigments and pearlescent pigments, and mixtures thereof.

3. The mascara system of claim 2, wherein at least some of the pigment particles are black iron oxide.

4. The mascara system of claim 1, further comprising a film-forming polymer.

5. The mascara system of claim 4, where the film-forming polymer is selected from the group consisting of polyvinylpyrolidone, polyvinyl alcohol, ammonium acrylate copolymers, polyurethane, trimethylsiloxysilicate, dimethicone, and hydrogenated polycyclopentadiene.

6. The mascara system of claim 1, wherein the fibers are organic fibers of synthetic origin.

7. The mascara system of claim 6, wherein at least some of the fibers are formed from a material selected from the group consisting of polyesters, polyurethanes, polyamides, acrylic polymers, and polyolefins.

8. The mascara system of claim 1, wherein at least some of the fibers are rigid fibers.

9. The mascara system of claim 8, wherein the fibers comprise a polyimideamide.

10. The mascara system of claim 1, wherein the fibers have a yarn count of between about 0.15 and about 30 denier.

11. The mascara system of claim 1, wherein the fibers are at least one of coated and treated.

12. The mascara system of claim 1, wherein the fibers have ends that are at least one of blunt and polished.

13. The mascara system of claim 1, wherein the fibers are hollow.

14. The mascara system of claim 1, wherein the fibers have a circular cross section.

* * * * *